(12) United States Patent
Chen et al.

(10) Patent No.: US 9,757,202 B2
(45) Date of Patent: Sep. 12, 2017

(54) METHOD AND SYSTEM OF DETERMINING PROBE POSITION IN SURGICAL SITE

(71) Applicants: Chieh-Hsiao Chen, Taichung (TW); Kuan-Ju Wang, Hsinchu County (TW)

(72) Inventors: Chieh-Hsiao Chen, Taichung (TW); Kuan-Ju Wang, Hsinchu County (TW)

( * ) Notice: Subject to any disclaimer, the term of this patent is extended or adjusted under 35 U.S.C. 154(b) by 211 days.

(21) Appl. No.: 14/784,846

(22) PCT Filed: Aug. 19, 2015

(86) PCT No.: PCT/CN2015/087500
§ 371 (c)(1),
(2) Date: Oct. 15, 2015

(87) PCT Pub. No.: WO2016/026437
PCT Pub. Date: Feb. 25, 2016

(65) Prior Publication Data
US 2016/0296291 A1 Oct. 13, 2016

Related U.S. Application Data

(60) Provisional application No. 62/039,412, filed on Aug. 19, 2014.

(51) Int. Cl.
A61B 90/11 (2016.01)
A61B 34/20 (2016.01)
A61B 90/00 (2016.01)

(52) U.S. Cl.
CPC .............. *A61B 34/20* (2016.02); *A61B 90/11* (2016.02); *A61B 90/36* (2016.02);
(Continued)

(58) Field of Classification Search
None
See application file for complete search history.

(56) References Cited

U.S. PATENT DOCUMENTS 6,167,295 A 12/2000 Cosman
9,271,682 B2 * 3/2016 Cerofolini .............. A61B 5/055
(Continued)

FOREIGN PATENT DOCUMENTS

| CN | 103040525 | 4/2013 |
|---|---|---|
| CN | 103230304 | 8/2013 |
| CN | 103284792 | 9/2013 |

OTHER PUBLICATIONS

The International Search Report and the written Opinion of the International Searching Authority, International Application No. PCT/CN2015/087500, International Filing Date: Aug. 19, 2015, dated Dec. 31, 2015, Applicant: Chen Chieh Hsiao et al, pp. 12.

(Continued)

*Primary Examiner* — Kim Vu
*Assistant Examiner* — Molly Delaney
(74) *Attorney, Agent, or Firm* — Haverstock & Owens LLP (57) ABSTRACT

One example method to determine a position of a probe in a surgical site with a plurality of reference structures may include receiving a three-dimensional image of the surgical site generated before the probe enters the surgical site and receiving a first two-dimensional image generated by the probe from a position within the surgical site. The three-dimensional image is associated with a first coordinate system, and the first two-dimensional image is associated with a second coordinate system. The method also includes acquiring registration to the plurality of reference structures based on the first two-dimensional image to obtain a permissible set of probe pose parameters, extracting a second two-dimensional image based on the permissible set of probe pose parameters from the three-dimensional image, and computing a correlation between the first two-dimensional image and the extracted second two-dimensional image to map the position of the probe represented by the (Continued)

second coordinate system to a position represented by the first coordinate system with respect to the three-dimensional image.

24 Claims, 10 Drawing Sheets

(52) U.S. Cl.
CPC . *A61B 2034/2065* (2016.02); *A61B 2090/364* (2016.02); *A61B 2090/365* (2016.02); *A61B 2090/3784* (2016.02)

(56) References Cited

U.S. PATENT DOCUMENTS

| | | | |
|---|---|---|---|
| 2004/0215071 A1* | 10/2004 | Frank | A61B 6/4441 600/407 |
| 2007/0167801 A1* | 7/2007 | Webler | G06F 19/3437 600/459 |
| 2007/0276234 A1 | 11/2007 | Shahidi | |
| 2008/0242978 A1 | 10/2008 | Simon et al. | |
| 2008/0262338 A1 | 10/2008 | Paitel et al. | |
| 2010/0239150 A1* | 9/2010 | Ishikawa | A61B 5/0095 382/131 |
| 2012/0010501 A1* | 1/2012 | Cerofolini | A61B 5/055 600/427 |
| 2013/0218024 A1* | 8/2013 | Boctor | A61B 34/20 600/476 |
| 2014/0018668 A1* | 1/2014 | Zheng | A61B 8/4254 600/424 |
| 2016/0035093 A1* | 2/2016 | Kateb | G06K 9/0014 382/131 |

OTHER PUBLICATIONS

International Preliminary Report on Patentability, Application No. PCT/CN2015/087500, International Filing Date: Aug. 19, 2015, Priority Filing Date: Aug. 19, 2014, dated Jul. 21, 2016, Applicant: Chen Chieh Hsiao et al, pp. 4.

* cited by examiner

1000 computer program product

1002 signal bearing medium

1004 at least one of one or more instructions for receiving a three-dimensional image of the brain generated before the probe enters the surgical site, wherein the three-dimensional image is associated with a first coordinate system;

one or more instructions for receiving a first two-dimensional image generated by the probe from a position within the surgical site, wherein the first two-dimensional image is associated with a second coordinate system;

one or more instructions for acquiring registration to the plurality of reference structures based on the first two-dimensional image to obtain a permissible set of probe pose parameters One or more instructions for extracting a second two-dimensional image (Slice Image from CT image) based on the permissible set of probe pose parameters from the three-dimensional image; and/or one or more instructions for computing a correlation between the first two-dimensional image and the extracted second two-dimensional image to map the position of the probe represented by the second coordinate system to a position represented by the first coordinate system with respect to the three-dimensional image

1006 communication medium

1008 computer readable medium

1010 recordable medium

Fig. 10

METHOD AND SYSTEM OF DETERMINING PROBE POSITION IN SURGICAL SITE

FIELD OF THE INVENTION

The present disclosure relates to a guiding and positioning system, and more particularly a method and system of determining the position of a probe in a surgical site during a surgical procedure.

BACKGROUND

Common brain diseases, such as brain tumors, Parkinson's disease and epilepsy, not only adversely affect the patients' quality of life but sometimes can also directly contribute to the patients' death. Invasive surgical procedures are usually performed after conservative treatments, such as medicines or physical therapies, failed to relieve the patients' symptoms. In such procedures, given the anatomy of the brain, a surgeon has limited space to maneuver a surgical instrument.

Currently, a surgeon can only rely on the pre-operative data before performing a brain surgery, but even the minor shift of the brain during the surgical procedure or the improper operation of the stereotactic positioning system often renders the position data of the surgical site inaccurate.

In addition, any pre-operative planned pathway based on the pre-operative data may change due to a number of factors, such as the movement of the patient's position, the change in the patient's condition, or the insertion of the surgical probe itself. Any such deviation from the pre-operative planned pathway often leads to further complications or an increased mortality rate.

SUMMARY

In accordance with one embodiment of the present disclosure, a method to determine a position of a probe in a surgical site with a plurality of reference structures is disclosed. The method includes receiving a three-dimensional image of the surgical site generated before the probe enters the surgical site and receiving a first two-dimensional image generated by the probe from a position within the surgical site. The three-dimensional image is associated with a first coordinate system, and the first two-dimensional image is associated with a second coordinate system. The method also includes acquiring registration to the plurality of reference structures based on the first two-dimensional image to obtain a permissible set of probe pose parameters, extracting a second two-dimensional image from the three-dimensional image based on the permissible set of probe pose parameters, and computing a correlation between the first two-dimensional image and the extracted second two-dimensional image to map the position of the probe represented by the second coordinate system to a position represented by the first coordinate system with respect to the three-dimensional image.

In accordance with one embodiment of the present disclosure, a machine-readable medium embodying a set of instructions, which in response to execution by a computing device, cause the computing device to determine a position of a probe in a surgical site is disclosed. The method includes receiving a three-dimensional image of the surgical site generated before the probe enters the surgical site and receiving a first two-dimensional image generated by the probe from a position within the surgical site. The three-dimensional image is associated with a first coordinate system, and the first two-dimensional image is associated with a second coordinate system. The method also includes acquiring registration to the plurality of reference structures based on the first two-dimensional image to obtain a permissible set of probe pose parameters, extracting a second two-dimensional image from the three-dimensional image based on the permissible set of probe pose parameters, and computing a correlation between the first two-dimensional image and the extracted second two-dimensional image to map the position of the probe represented by the second coordinate system to a position represented by the first coordinate system with respect to the three-dimensional image.

In accordance with one embodiment of the present disclosure, a system configured to determine a position of a probe in a surgical site with a plurality of reference structures is disclosed. The system includes a processor, a first table, a second table, and a memory. The memory embodies a set of executable instructions, which in response to execution by the processor, cause the processor to acquire registration to the plurality of reference structures based on a first two-dimensional image generated by the probe from a position within the surgical site during a surgical procedure and a three-dimensional image of the surgical site before the surgical procedure to obtain a permissible set of probe pose parameters, wherein the three-dimensional image is associated with a first coordinate system, and the first two-dimensional image is associated with a second coordinate system, extract a second two-dimensional image from the three-dimensional image based on the permissible set of probe pose parameters, select a first set of pixels from the first two-dimensional image using the first table, select a second set of pixels from the extracted second two-dimensional image using the first table and the second table and based on one of the permissible set of probe pose parameters, and compute a correlation between the first set of pixels and the second set of pixels to map the position of the probe represented by the second coordinate system to a position represented by the first coordinate system with respect to the three-dimensional image.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

This disclosure is drawn, inter alia, to methods, apparatuses, and systems related to determine the position of a probe in a surgical site during a surgical procedure. Throughout the disclosure, the terms "three-dimensional image" and "volume image" are used interchangeably.

Figure 1:
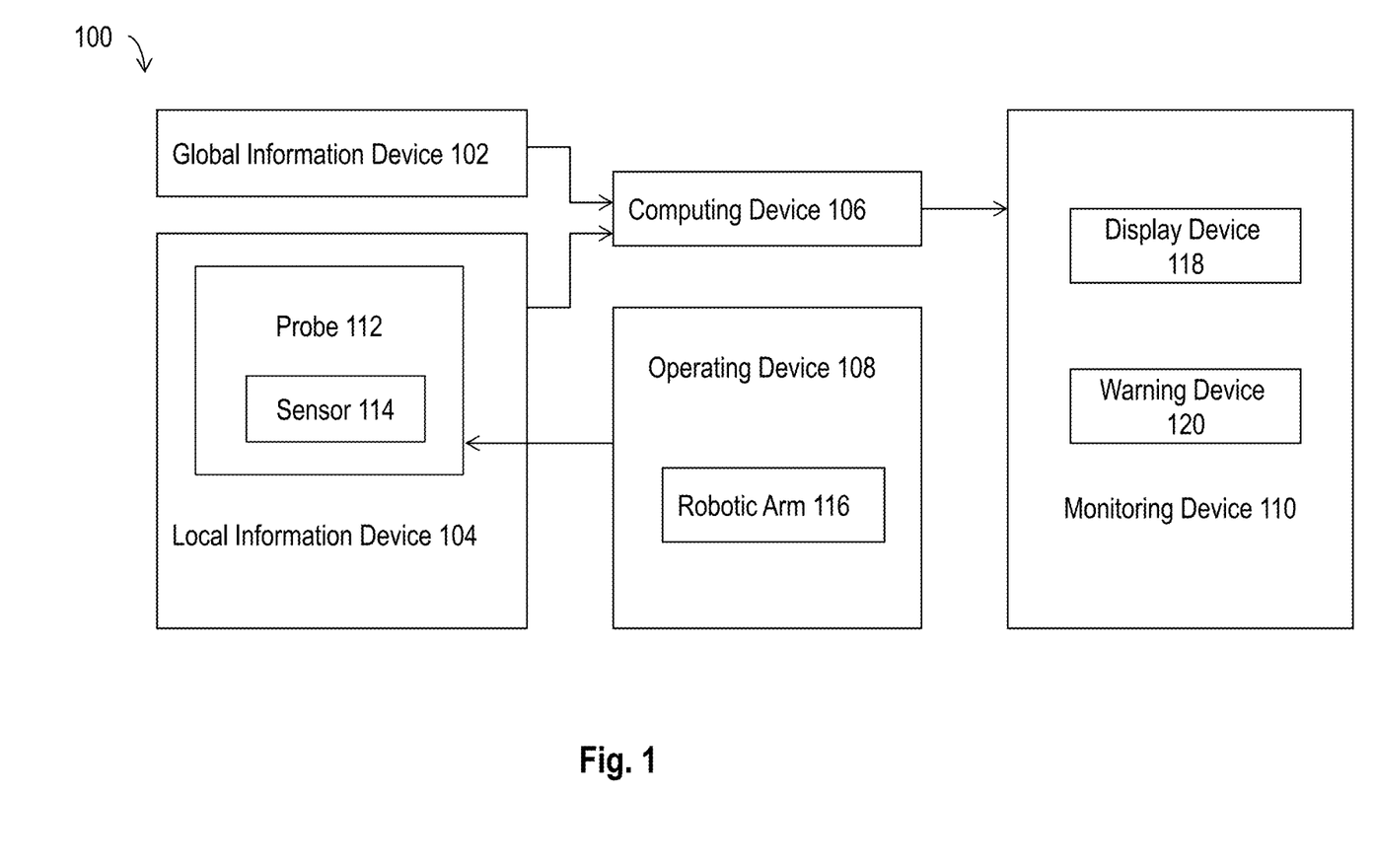
FIG. 1 is block diagram showing the configuration of a surgical guiding and positioning system.

FIG. 1 is block diagram showing the configuration of a surgical guiding and positioning system 100, in accordance with one embodiment of the present disclosure. The surgical guiding and positioning system 100 mainly includes a global information device 102, a local information device 104, a computing device 106, a monitoring device 108, and an operating device 110.

The global information device 102 is capable of collecting overall information of a surgical site, such as a brain, before a surgical procedure begins. In some embodiments, the overall information can be acquired through computed tomography (CT), magnetic resonance imaging (MRI), surface scan, X-ray scan, ultrasound scan, and etc. With the overall information (e.g. the intracranial anatomy, the target or lesion location, or the surface land markings) of the surgical site, a surgeon may plan a surgical pathway before a surgical procedure begins.

One embodiment of the local information device 104 includes a probe 112 with at least one sensor 114 directly disposed on the probe 112.

A surgeon may also control the probe 112 via the operating device 108. One embodiment of the operating device 108 may include a robotic arm 116 via which the surgeon can control the probe 112.

During the surgical procedure, the one or more sensors 114 disposed on the probe 112 are configured to obtain local data near the probe 112 itself. This collected local data, in conjunction with the global data from the global information device 102, may be processed by the computing device 106.

In one embodiment, the computing device 106 is capable of determining a position data of the probe 112 in the surgical site in relation to the global data. The global data is obtained before the surgical procedure begins, and the local data is obtained during the surgical procedure. Additional details will be provided in subsequent paragraphs.

One embodiment of the monitoring device 110 includes a display device 118 and a warning device 120. The display device 118 is capable of displaying a 3D image based on the aforementioned overall information from the global information device 102 before the surgical procedure begins. During the surgical procedure, the display device 118 is capable of displaying a real-time position of the probe 112 superimposed on the 3D image based on the position data calculated by the computing device 106. In such an embodiment, a surgeon may learn the real-time position of the probe 112 relative to the 3D image and adjust the procedure accordingly.

One embodiment of the warning device 120 is capable of sending out a real-time warning to a surgeon when a blood vessel or vital area is nearby, when the probe 112 is in a target position or a risky position, or the probe 112 deviates from the planned surgical pathway.

Figure 2:
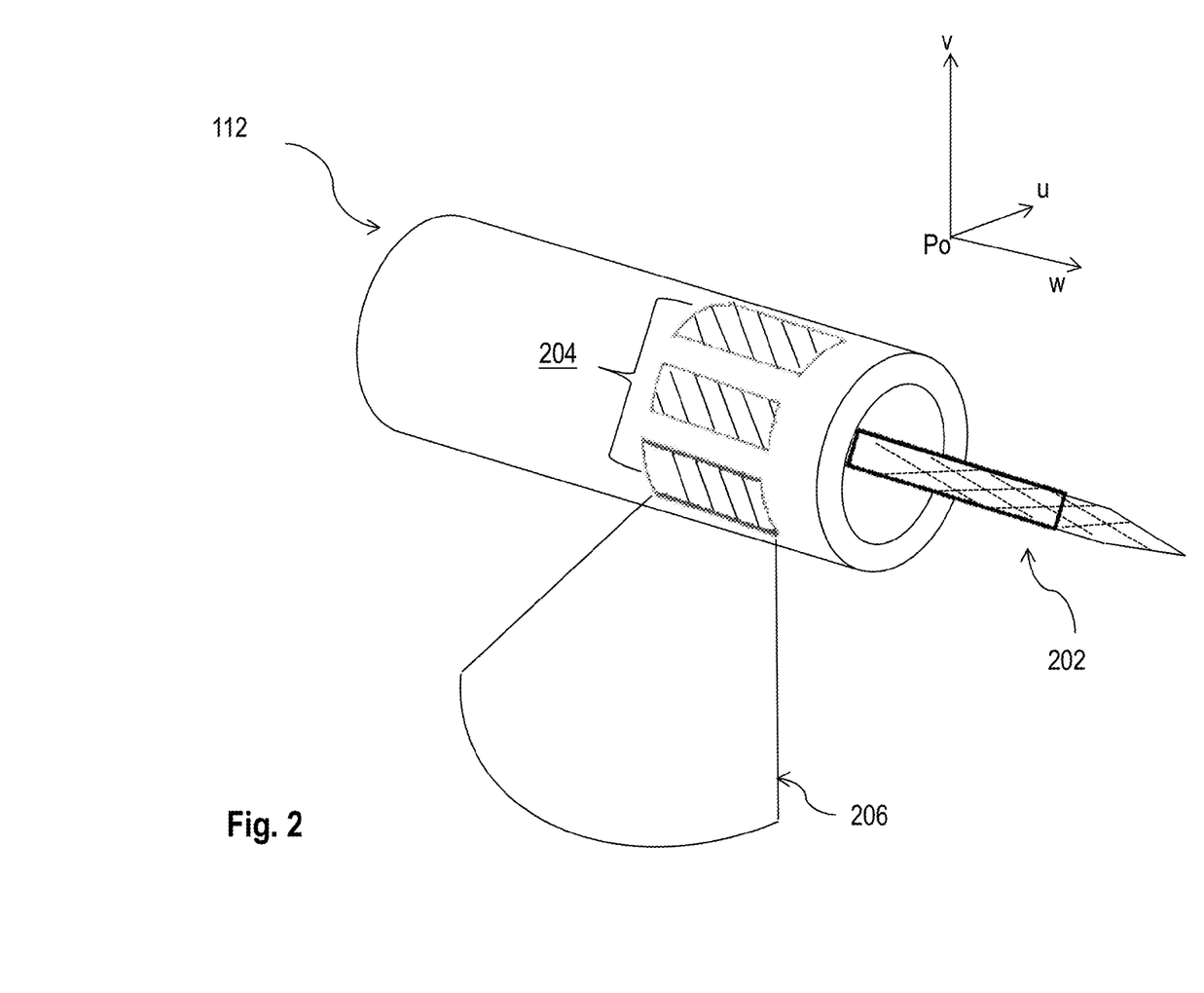
FIG. 2 is a schematic view showing an example arrangement of one or more sensors on a probe.

FIG. 2 is a schematic view showing an example arrangement of one or more sensors on a probe, such as the probe 112 of FIG. 1, in accordance with one embodiment of the present disclosure. One embodiment of the probe 112 may be configured as a sheath that wraps around a surgical device 202, and the surgical device 202 is moveable therein. Some examples of the surgical device 202 may include, without limitation, a biopsy needle, a biopsy forceps, a clamp, a laser fiber, a brain pressure monitor catheter, and others.

The probe 112 includes one or more sensors 204. An example of the sensor 204 may be an ultrasound transducer with varying detection ranges. In one embodiment, the probe 112 may include eight sensors 204, spaced every 45 degrees around the circumference of the probe 112. Each of the sensors 204 may be configured to collect and generate a two-dimensional (2D) image 206 in a plane that includes the probe 112 (e.g., w axis). The data that the probe 112 collects and generates, in one embodiment, are associated in one coordinate system (e.g., u,v,w, with the w axis aligned with the axis of the probe 112).

In one embodiment, the ultrasonic transducers are configured to transmit pulses of ultrasound into tissues and/or anatomical parts that are within the ultrasound range of the transducers. The ultrasound may echo off the tissues and/or anatomical parts, with different types of tissues and anatomical parts reflecting varying degrees of sounds. The echoes are recorded and displayed as the 2D image 206. Since the signal strength associated with bones is generally stronger than the signal strength associated with the soft brain tissues, to prevent the bone signal from overpowering the tissue signal, the ultrasound range may be adjusted, so that the generated ultrasound images may reveal more information associated with the soft brain tissues, which may include the target tissues and other vital tissues in the surgical procedure.

Figure 3:
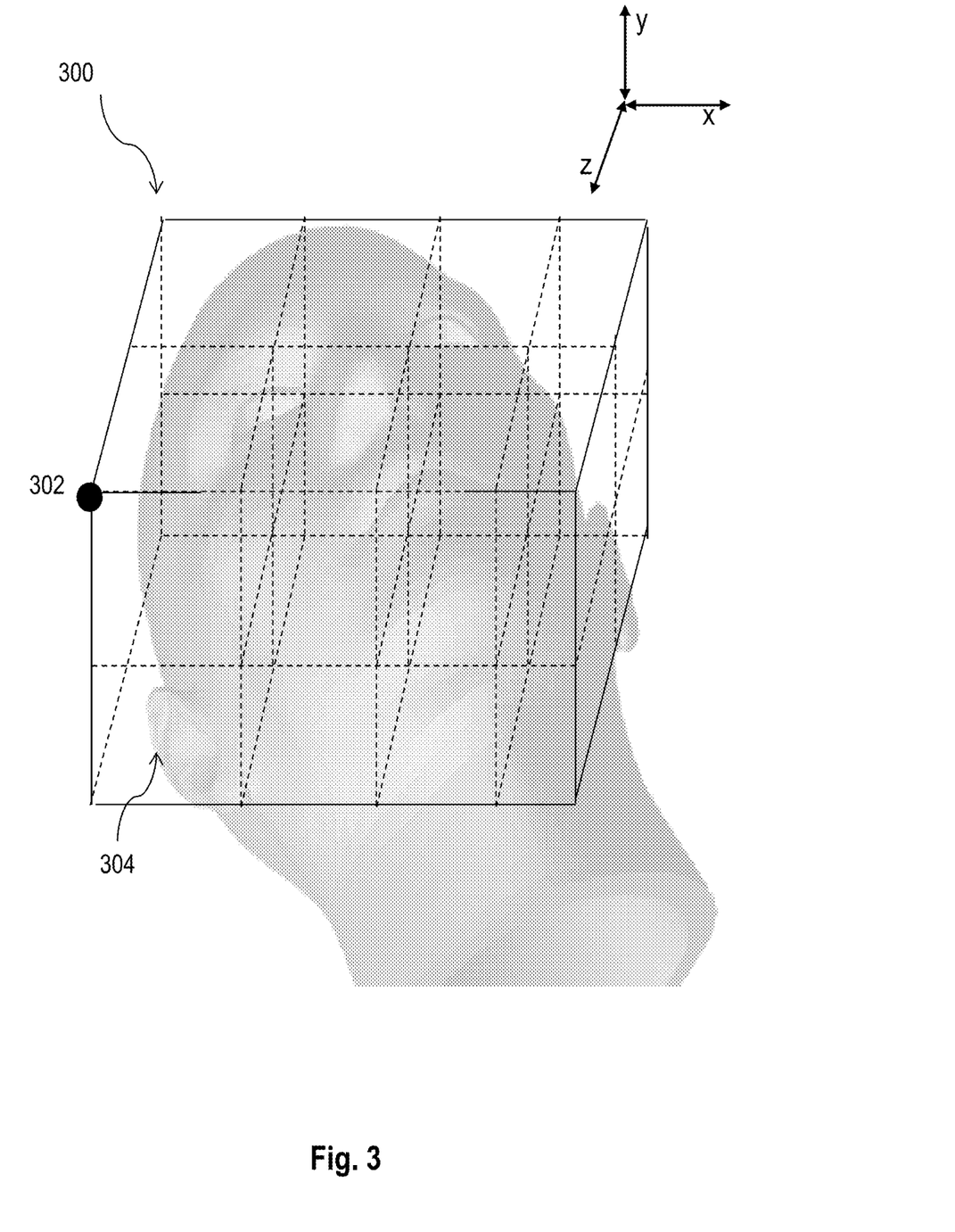
FIG. 3 shows an example three-dimensional image of a patient's head prior to performing a surgical procedure.

FIG. 3 shows an example three-dimensional (3D) image 300 of a patient's head prior to performing a surgical procedure. To illustrate, suppose the 3D image 300 is a CT image. Prior to operation, the 3D image 300 may be ordered by the surgeon, so that the position of the target area with respect to other tissues or structures in the brain can be first evaluated, and a surgical pathway can be planned. The 3D image 300 includes voxels, each of which represents a value on a grid in 3D space. Here, the voxels are shown to be arranged in a perceptible cube with an origin 302.

In one embodiment, the 3D image 300 is associated with one coordinate system (e.g., x,y,z). For example, with the origin 302 having coordinates (0, 0, 0), the coordinates for a voxel 304 in the 3D image 300 (e.g., $X_1$, $Y_1$, $Z_1$) in the same coordinate system may be obtained.

Figure 4:
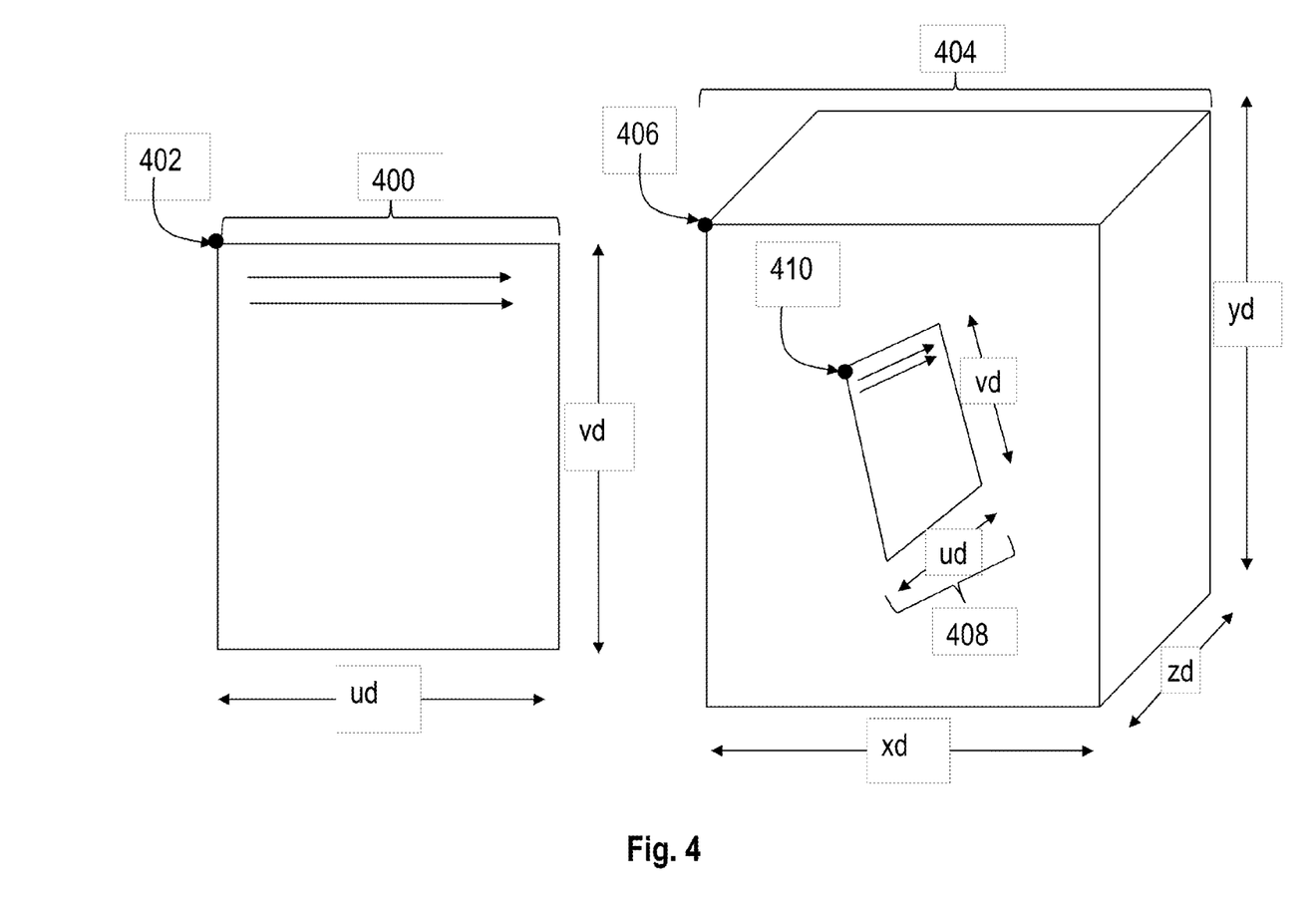
FIG. 4 is a simplified block diagram illustrating the extracting of a two-dimensional image from a volume image.

To determine where the 2D image data captured and generated by the probe 112 of FIG. 1 and FIG. 2 in one coordinate system (e.g., u,v,w) can be appropriately placed in the 3D image data shown in FIG. 3 in another coordinate system (e.g,. x,y,z), one approach is to extract a 2D image from the 3D image data and compare the extracted 2D image with the 2D image from the probe 112. FIG. 4 is a simplified block diagram illustrating the extracting of a 2D image from a volume image, in accordance with one embodiment of the present disclosure. A 2D image 400, with an origin 402, may correspond to the 2D image 206 of FIG. 2. A volume image 404, with an origin 406, may correspond to the 3D image 300 and the origin 302 of FIG. 3, respectively.

As discussed earlier, since the 2D image 400 corresponds to a 2D image that the probe 112 of FIG. 1 and FIG. 2 captures and generates at a certain position and orientation in the surgical site (e.g., brain) during a surgical procedure, and the volume image 404 corresponds to the 3D image of the same surgical site before the surgical procedure begins, the position and orientation of the probe 112 at which the 2D image 400 is collected and generated becomes relevant in identifying the appropriate point in the volume image 404 to extract a 2D image 408 from. For simplicity, suppose the origin 402 is determined to map to an origin 410 in the volume image 404. In one embodiment, as shown in FIG. 4, the size and/or the raster scan sequence of the 2D image 400 may be used to extract the 2D image 408. For instance, the voxel positions in the volume image 404 may be located in a manner, so that they correspond to a raster scan of the 2D image 400. In some other embodiments, corrections may be made by interpolating to intermediate points between data points represented by the voxels, because the pixels of the extracted 2D image 408 generally may not align exactly with the voxels of the volume image 404.

With the extracted 2D image 408, comparisons can be made between the 2D image 400 and the 2D image 408 to determine whether there is a high correlation between the two images. If the correlation is high, then there is higher confidence that the mapping between the 2D image 400 and the 2D image 408 is sufficiently accurate. If the mapping is sufficiently accurate, then a surgeon would be able to evaluate the data nearby the probe 112, which are likely the data along the planned surgical pathway, in view of the volume image 404 as the surgical procedure is being performed. Local deformation, including translational and rotation shifts and shear distortion in tissues, in the surgical site can thus be estimated and taken into consideration during the surgical procedure.

Although the 2D image 400 and the extracted 2D image 408 are shown in a square-like shape, it should be apparent to a person skilled in the art to recognize that these images can be in any shape (such as a fan slice shown in FIG. 2) that is practical to implement.

Figure 5:
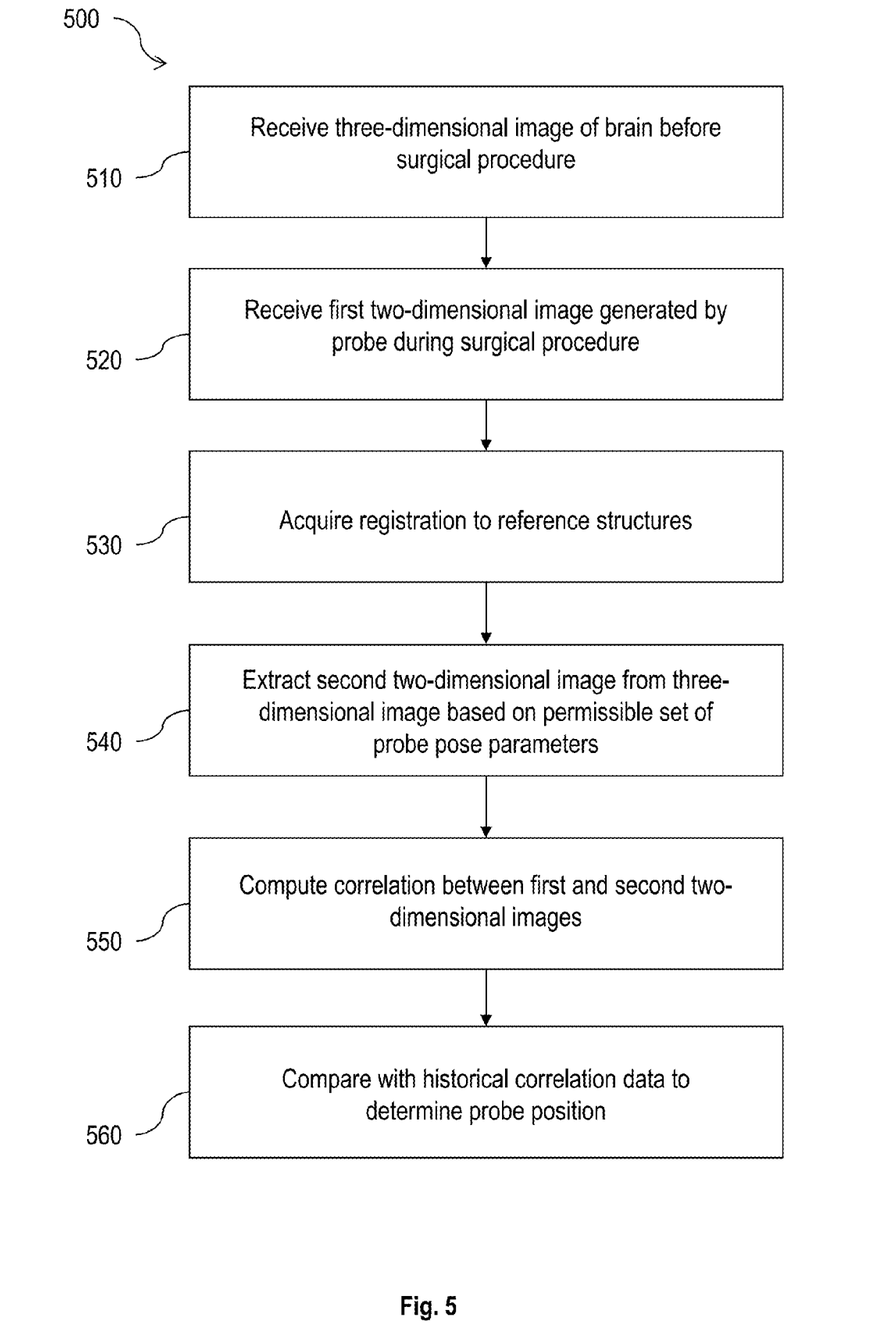
FIG. 5 is a flow diagram illustrating an example process of determining the position of a probe during a surgical procedure.

FIG. 5 is a flow diagram illustrating an example method 500 to determine the position of a probe during a surgical procedure, in accordance with one embodiment of the present disclosure. The process 500 may include one or more operations, functions, or actions as illustrated by blocks 510, 520, 530, 540, 550, and/or 560, which may be performed by hardware, software and/or firmware. The various blocks are not intended to be limiting to the described embodiments. For example, one skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Processing for the method 500 may begin at block 510, "receive three-dimensional image of surgical site before surgical procedure." For example, before the surgical procedure, some medical imaging techniques may be used to capture a snapshot of the patient's conditions, so that an operation plan may be formulated. Suppose the surgical site is the brain of the patient. The surgeon may order a CT scan of the brain. In conjunction with FIG. 1 and FIG. 2, the computing device 106 may receive this 3D volume image of the patient's brain from the global information device 102 (e.g., CT scanner). In addition to soft brain issues, the 3D volume image may also include voxels that represent reference structures, such as, without limitation, the skull of the patient or a base plate coupled to the skull.

Block 510 may be followed by block 520, "receive first two-dimensional image generated by probe during surgical procedure." Here, after the surgical procedure begins, the computing device 106 may be configured to receive a first 2D image generated by the probe 112. As mentioned above, in one embodiment, the sensors, or the ultrasound transducers, disposed on the probe 112 may be configured to capture and generate 2D images from the position and orientation of the probe 112 in the brain.

Block 520 may be followed by block 530, "acquire registration to reference structures," where the acquisition of registration broadly refers to the determination of one-to-one mapping between one set of coordinates in one coordinate system to another set in another coordinate system, such that the data in the two coordinate systems that correspond to the same anatomical part are mapped to one another. Some examples of the reference structures include, without limitation, the bone and certain soft tissues. To acquire registration to such reference structures may involve an iterative process, where different types of searches are performed based on varying sets of pose parameters (e.g., x,y,z,pitch, yaw,roll) of the probe 112 and varying search parameters (e.g., the ultrasound range). In one embodiment, one output of the registration acquisition operation is one or more permissible sets of pose parameters in the coordinate system of the 3D volume image. In other words, after having acquired registration to the reference structures, the set of possible coordinates in the coordinate system of the 3D volume image that could map to the location of the probe 112 within the brain becomes more defined. A more detailed description of this registration acquisition process is set forth in subsequent paragraphs.

Block 530 may be followed by block 540, "extract second two-dimensional image from three-dimensional image based on permissible set of probe pose parameters." As discussed earlier and in conjunction with FIG. 4, with the coordinates in the coordinate system of the volume image, the second 2D image, such as the 2D image 408, can be extracted.

Block 540 may be followed by block 550, "compute correlation between first and second two-dimensional images." A high correlation between the two images would signal that the selected pose parameters for the probe 112 results in a fairly accurate mapping between the two coordinate systems, and the surgeon may rely on the extracted 2D image to evaluate the surgery.

Block 550 may be followed by block 560, "compare with historical correlation data to determine probe position." Here, in one embodiment, the best correlation score out the previously computed correlation scores and the associated pose parameters of the probe are maintained. If a newly computed correlation score is higher (i.e., the two images are even more highly correlated), then the newly computed correlation score and the associated pose parameters are kept.

In one embodiment, to ensure the best computed correlation score is obtained, all of the permissible set of probe pose parameters may be used to obtain the different 2D images and to compute different correlation scores. Also, for each of the sensors disposed on the probe 112, a different 2D image is captured and generated from different orientations. All of these different 2D images are compared with their corresponding extracted 2D images, and the correlation scores may be accumulated. Moreover, consistency constraints may be imposed. One constraint may allow the probe to move continuously along a mostly linear path. Another constraint may allow the probe to rotate about its axis.

Figure 6:
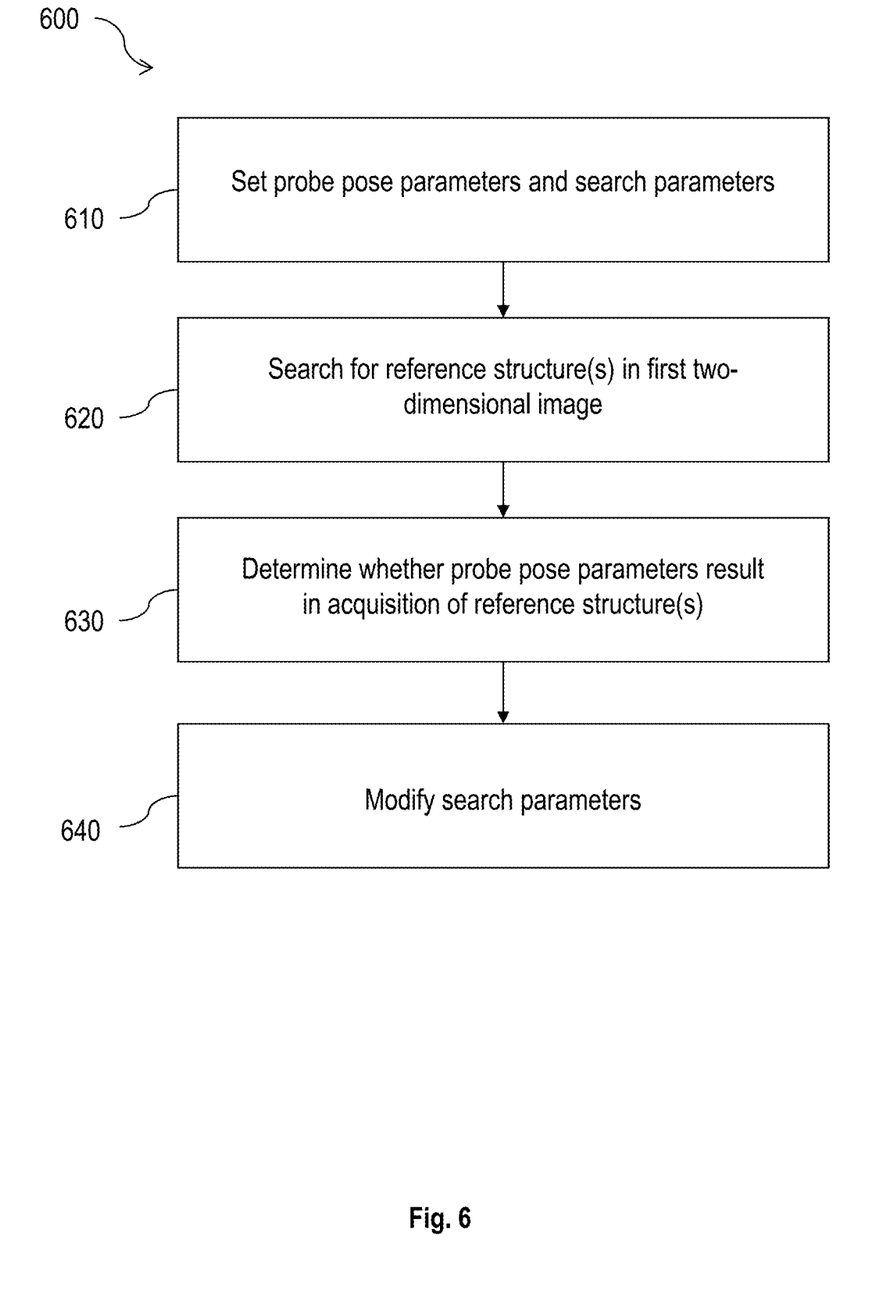
FIG. 6 is a flow diagram illustrating an example method 600 to acquire registration to reference structures.

FIG. 6 is a flow diagram illustrating an example method 600 to acquire registration to reference structures, in accordance with one embodiment of the present disclosure. The process 600 may include one or more operations, functions, or actions as illustrated by blocks 610, 620, 630, and/or 640, which may be performed by hardware, software and/or firmware. The various blocks are not intended to be limiting to the described embodiments. For example, one skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Processing for the method 600 may begin at block 610, "set probe pose parameters and search parameters." In one embodiment, one initial probe pose parameters may be set based on surgical preplanning and/or mechanical constraints (e.g., relative to a base plate coupled to the patient's skull). One initial set of search parameters may include, without limitation, search interval, increment sizes for each pose parameter, ultrasound range limit, and others.

Block 610 may be followed by block 620, "search for reference structure(s) in first two-dimensional image." In one embodiment, the initial ultrasound range limit is set to be larger, so that a more exhaustive search in the first 2D image (the 2D image captured/generated by the probe, such as the 2D image 400 of FIG. 4) to identify the reference structure(s) may be performed.

Block 620 may be followed by block 630, "determine whether probe pose parameters result in an acquisition of identified reference structure(s)." In other words, with the probe pose parameters set to certain values, one iteration of the method 600 is to determine whether an agreement can be found between the identified reference structure(s) in the first 2D image and the corresponding reference structure(s) in the volume image. If an agreement is found, then the set of probe pose parameters leading to the registration of the reference structure(s) are maintained. Otherwise, the probe pose parameters may be set to different values and block 630 is performed again to determine whether the agreement can be found.

Suppose registration to one reference structure, such as the bone, is acquired in block 630. Block 630 may be followed by block 640, "modify search parameters." In one embodiment, the ultrasound range limit, as one of the search parameters, may be reduced, so that the soft tissue near the probe 112 may be considered. Different ultrasound range limits may also be utilized, so that different distances from the probe 112 may be measured.

In one embodiment, the computing device 106 of FIG. 1 may be configured to perform the method 500 and the method 600. To achieve more meaningful results and before some of the aforementioned operations are performed, the computing device 106 may be configured to process the 3D volume image, the first 2D image, and/or the extracted second 2D image.

Bones are associated with stronger signals than soft brain tissues in both CT and ultrasound images. In one embodiment, the computing device 106 may utilize this signal strength difference between the bone and the soft brain tissues to differentiate the pixels representing the skull and the pixels representing the soft brain tissues in the first 2D image and the extracted second 2D image. Computing the correlation between just the pixels representing the soft brain tissues in the two 2D images may result in more meaningful comparisons.

More specifically, in one embodiment, the pixels in the 2D image extracted from the volume image representing the bone may be assigned a first value, and the pixels in the same extracted image representing parts other than the skull may be assigned a second value. If a pixel value is closer to the first value than the second value, then it may be more likely that such a pixel represents a part in proximity to the skull but further away from the soft brain tissues. In addition, a mask may be applied to the extracted 2D image to select pixels with an assigned value below a threshold to suppress the strong signal associated with the skull.

In one embodiment, the computing device 106 may apply a spatial bandpass filter, such as the Laplacian of Gaussian (LOG) convolution, to the first 2D image to suppress finer and coarser textures before the correlation between the first 2D image and the second extracted 2D image is computed (e.g., block 550 of FIG. 5). The filter 2D image may have a substantial zero mean with swings both positive and negative. The boarders between positive and negative regions in the LOG filtered image occur at locations where transitions occur in the original image. In addition, the regions of positive and negative may be centered between the transition regions and are generally stable. Such regions can be used to acquire registration between images of the same subject matter even with significant differences in the image capture/generation mechanism such as in the case with ultrasound images and CT volume images or ultrasound images and MRI volume images.

In one embodiment, a LOG convolution may be applied to the second extracted 2D image. Alternatively, the LOG convolution may also be applied to the volume image before the second 2D image is extracted from the volume image. A two-dimensional image extracted from the LOG-processed volume image may be similar to the second extracted 2D image that is LOG-processed.

In one embodiment, a Hounsfield Units remapping approach may be applied to the second extracted 2D image. The Hounsfield Units remapping approach includes remapping Hounsfield Units to different value ranges to enhance the tissue impedances. For example, the Hounsfield Unit ranges associated with brain gray matters may be assigned to a larger value range than the Hounsfield Unit ranges associated with brain white matter.

Since ultrasound images normally contain significant speckle artifact, in one embodiment, the speckle artifact is filtered out of the ultrasound images before subsequent processing. One example filter has a zero amplitude at a radial frequency proportional to the frequency of the ultrasound image. In another embodiment, the filter is a frequency-domain filter. In yet another embodiment, the filter is a sinc function of the radial frequency coordinate:

$$\mathrm{sinc}(f_r/f_s) = \frac{\sin f_r/f_s}{f_r/f_s}$$

In another embodiment, the scale frequency $f_s$ is chosen to give a zero amplitude at a desired radial frequency.

Figure 7:
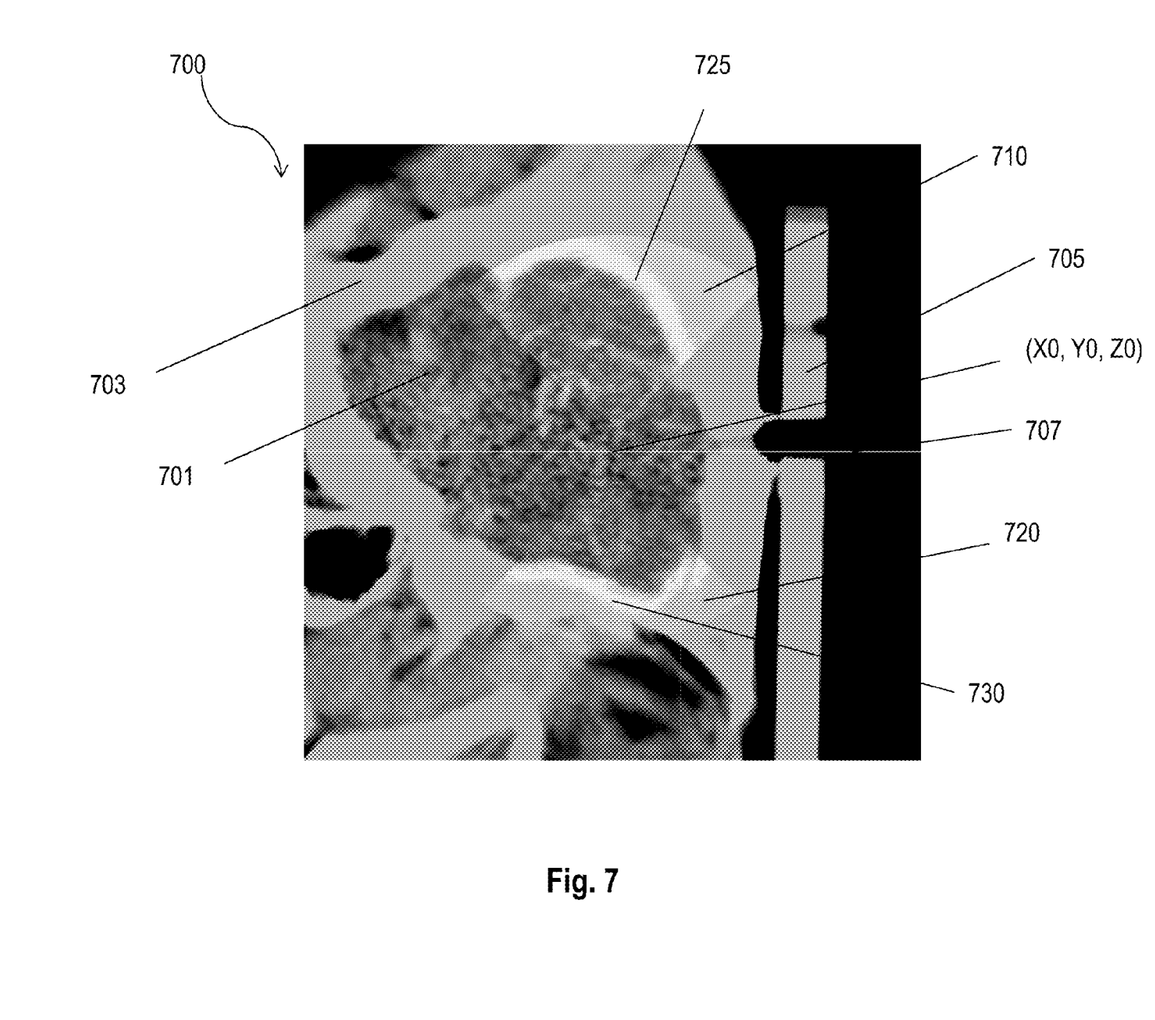
FIG. 7 shows an example display with ultrasound images superimposed on a slice image extracted from a CT volume image.

Referring back to FIG. 5, with the probe position determined in block 560, in one embodiment, the first 2D image (e.g., the 2D image 400 of FIG. 4) and the second extracted 2D image (e.g., the extracted 2D image 408) may be displayed on the display device 118. FIG. 7 shows an example display with ultrasound images 710 and 720 superimposed on a slice image 700 extracted from a CT volume image, in accordance with one embodiment of the present disclosure. Here, the ultrasound images 710 and 720 are captured and generated from a certain location of a probe in the brain, which corresponds to a set of coordinates (e.g., the coordinates $(X_0, Y_0, Z_0)$) in the coordinate system associated with the CT volume image. According to the coordinates $(X_0, Y_0, Z_0)$, the slice image 700 is extracted from the CT volume image.

The slice image 700 shows soft tissues 701 (the region with darker shading) confined in a skull 703 (the region with lighter shading), a base plate 705 (the vertical bar), and a probe axis 707 (the white line through the center) for this slice image. Regions 725 and 730 show that the image rendered by the pixels representing the skull 703 in the slice image 700 are substantially similar with the image rendered by the pixels representing the skull 703 in the ultrasound image 710. The substantially similarity suggests that the pixels representing the skull 703 in the slice image 700 and the pixels representing the skull 703 in the ultrasound image 710 correspond to the same part of the skull 703. With the match of the skull anatomy, the position of coordinates $(X_0, Y_0, Z_0)$ with respect to the skull 703 may be determined.

Figure 8:
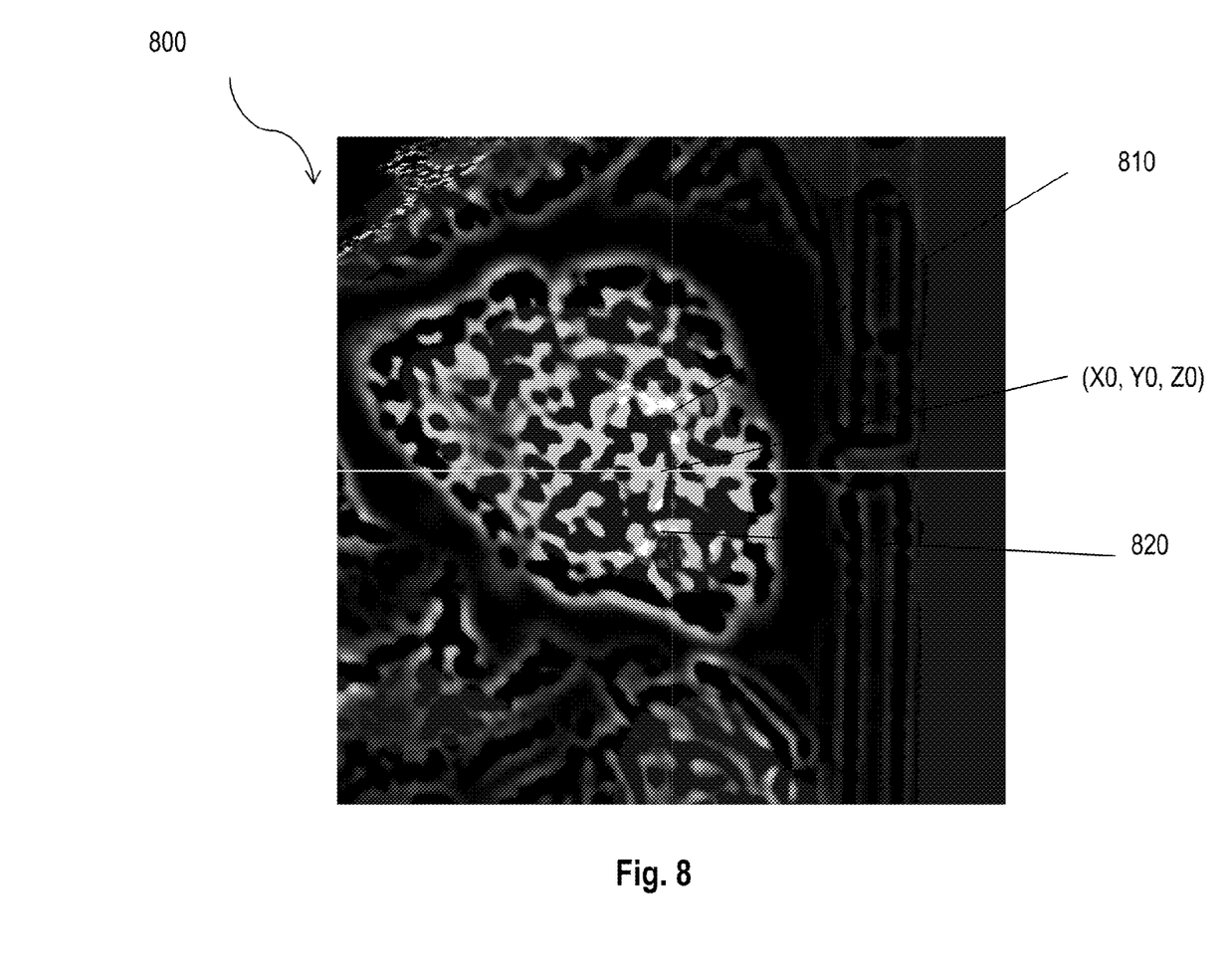
FIG. 8 shows an example display with filtered ultrasound images superimposed on a slice image extracted from a processed CT volume image.

FIG. 8 shows an example display with filtered ultrasound images 810 and 820 superimposed on a slice image 800 extracted from a processed CT volume image in accordance with one embodiment of the present disclosure. Although the filtered ultrasound images 810 and 820 are taken from the same coordinates $(X_0, Y_0, Z_0)$ of FIG. 7, the range of the filtered ultrasound images 810 and 820 is more limited than the range of ultrasound images 710 and 720, so that ultrasound images 810 and 820 do not include the skull and do not have the regions 725 and 730 shown in FIG. 7. Also, in this figure, the voxel values of the CT volume image have been changed to accentuate soft brain tissues by masking bone boundaries. As a result, the slice image 800 only includes pixels representing the soft brain tissues, and none for the skull. The pixels representing the soft brain tissues in the slice image 800 may be compared to the pixels representing the soft brain tissues in the ultrasound images 810 and 820. Also, correlation between the images rendered by the pixels representing the soft brain tissues in the slice image 800 and the images rendered by the pixels representing the soft brain tissues in the ultrasound image 810 and 820 may be computed. Assuming the slice image 800 and the ultrasound images 810 and 820 are highly correlated, differences between the slice image 800 and the ultrasound images 810 and 820 would correspond to the shift of the soft brain tissues. With high confidence in this determination, the surgeon is enabled to determine whether the target tissues or other vital tissues in the surgical procedure are shifted and take appropriate actions during the procedure.

Figure 9:
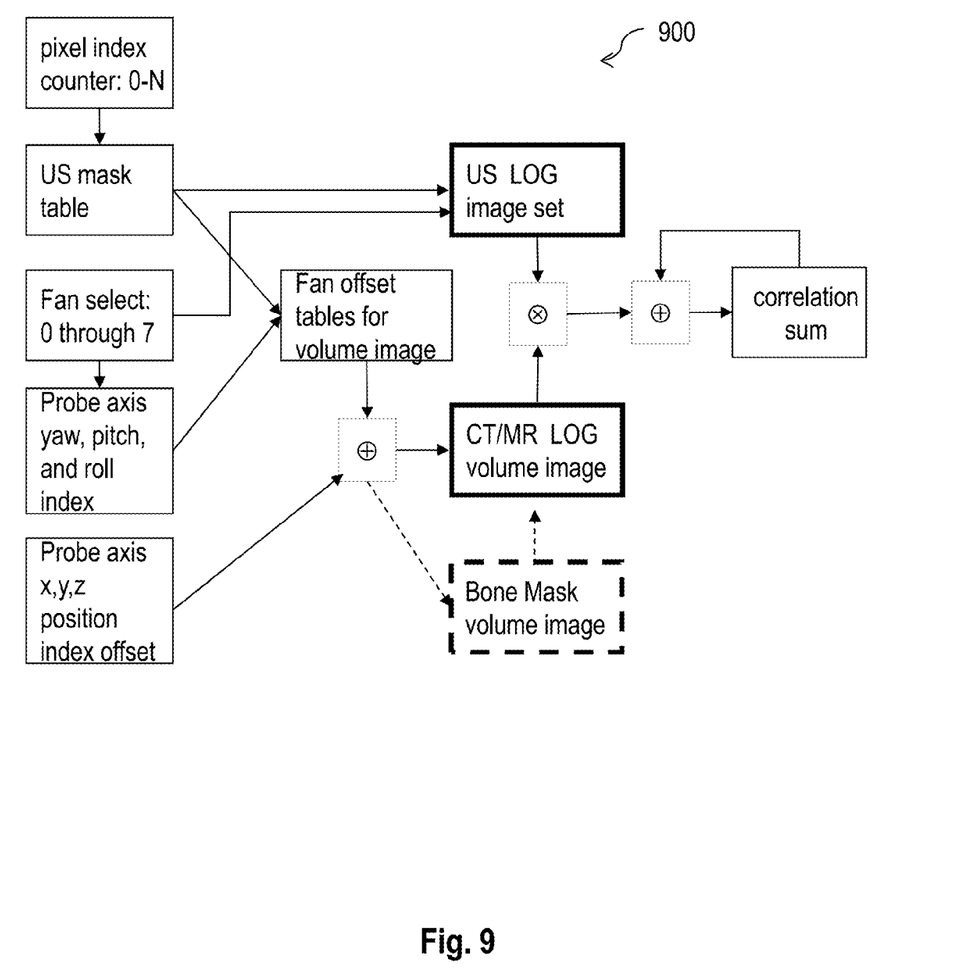
FIG. 9 is a block diagram of an example table-based system configured to compute a multi-dimensional correlation surface.

FIG. 9 is a block diagram of an example table-based system 900 configured to compute a multi-dimensional correlation surface, in accordance with one embodiment of the present disclosure.

The value N is the total number of pixels that will be correlated. N generally is smaller than the number of pixels in the ultrasound image. This is because pixels beyond a set range from the ultrasound probe are not used, likewise pixels closer than a given range are also ignored.

The US mask table contains a list of length N of the memory addresses (offsets from the beginning of the ultrasound image) of pixels that will be used for the correlation. This list follows a raster scan order. This offset output is also fed to the fan offset table for selecting the associated voxel addresses in the volume image.

The Fan offset tables are a collection of $k=k_1*k_2*k_3$ fan slice offset tables where:

$k_1$ is the number of roll orientations (typically 720 for half degree resolution)

$k_2$ is the number of yaw orientations relative a nominal probe direction perpendicular to the head plate (typically 40 for a range of ±10 degrees with half degree resolution).

$k_3$ is the number of pitch orientations relative a nominal probe direction perpendicular to the head plate (typically 40 for a range of ±10 degrees with half degree resolution).

Each of the k fan slice tables has a list of offset addresses that scans a raster pattern over a fan slice plane in the 3-D image volume. This raster scan has the same dimensions as the ultrasound images. Thus in operation, the Fan select and Probe axis yaw, pitch and roll boxes provide inputs to the Fan offset tables box to select one of the k fan slice offset tables. This selected table receives input from the US mask table and outputs an offset address for the 3-D volume image.

This offset address is summed ($\oplus$) with a fixed offset address from the Probe axis xyz position index offset box. This fixed offset translates the fan slice in the image volume. The output of the adder is then fed to the volume image memory where a value is accessed and output to the correlation multiplier ($\otimes$).

The correlation multiplier receives pixel values from the ultrasound image and the volume image. It multiplies those values and feeds the result to an accumulator.

This entire process is repeated N times as the counter module at the upper left steps through its count from 0 to N−1. At the end of this count the accumulator at the far right will contain a correlation sum for the six input parameters: fan index, roll, pitch, yaw, x, y, and z. A combined correlation for all 8 fan slices is computed by incrementing the Fan select register through its range.

By varying the six parameters searching for the best correlation this mechanism can be used to find the pose of the probe in the image volume that gives the best agreement between the pre-recorded volume image and real-time ultrasound images.

The system 900 may optionally include a bone mask volume image, so that bone regions may be excluded from the correlation calculation. In one embodiment, the bone mask volume image includes voxels that indicate whether the corresponding voxel in the CT/MRI LOG volume are soft tissue or bone. This bone mask volume is accessed in parallel with the LOG volume to determine whether or not to allow the accessed LOG voxel to contribute to the correlation sum. In one embodiment, the mask volume image is derived from the original CT/MRI volume image using a modality appropriate technique to identify bone voxels. Those voxel values are set to 1.0 and non-bone voxels are set to 0.0. A filter means is then applied to the volume marked with ones and zeros so that locations marked as soft tissue which are near bone get a value greater than zero and less than one. Furthermore locations closer to bone get a value closer to one. This allows a threshold to be used to select voxels that are at least a specified distance from the nearest bone voxel.

Figure 10:
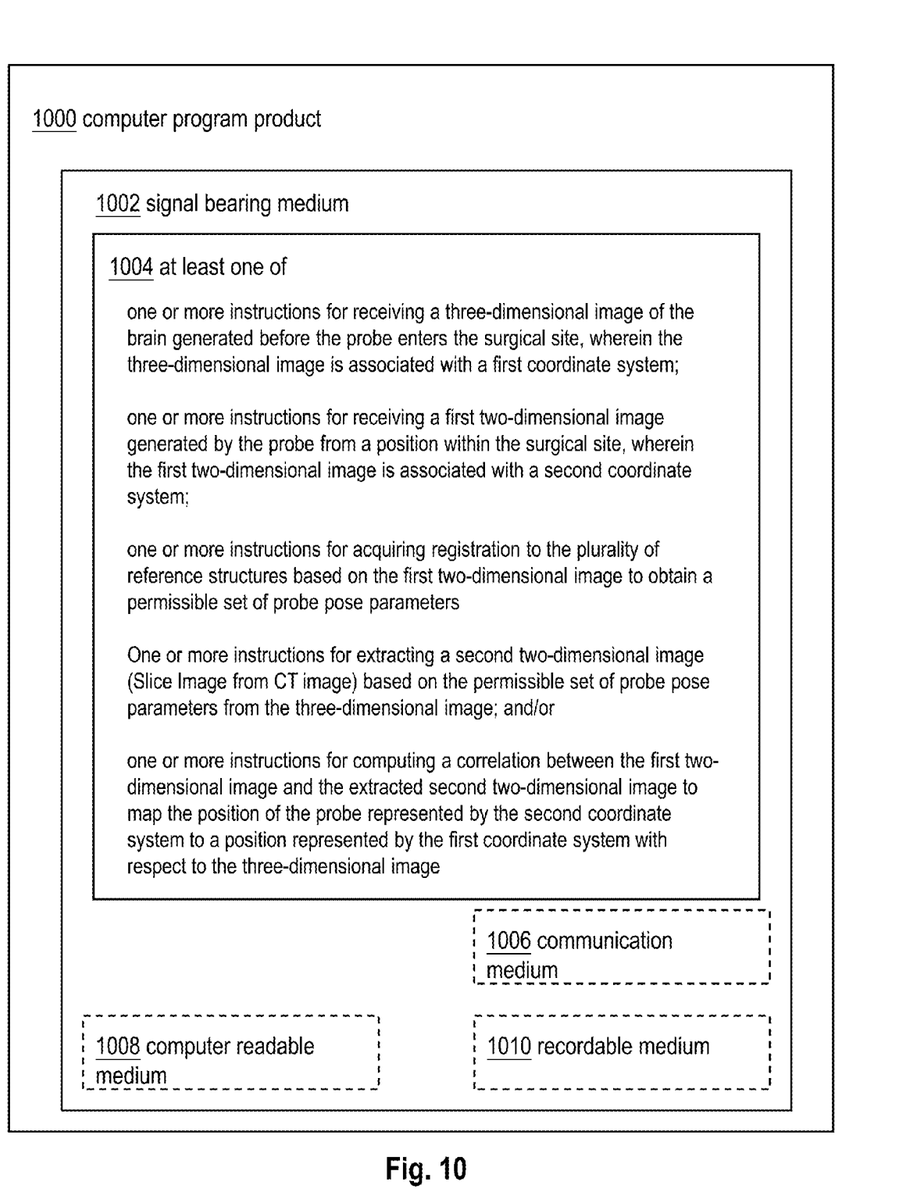
FIG. 10 is a block diagram illustrating a computer program product to implement a method to determine a position of a probe in a surgical site, all arranged in accordance with at least some embodiments described herein.

FIG. 10 is a block diagram illustrating a computer program product 1000 to implement a method to determine a position of a probe in a surgical site, in accordance with one embodiment of the present disclosure. The computer program product 1000 may include a signal bearing medium 1002. Signal bearing medium 1002 may include one or more sets of executable instructions 1004 stored thereon that, in response to execution by, for example, the computing device 106 of FIG. 1, may provide the features and operations described above.

In some implementations, the signal bearing medium 1002 may encompass a non-transitory computer readable medium 1008, such as, but not limited to, a hard disk drive, a Compact Disc (CD), a Digital Versatile Disk (DVD), a digital tape, memory, etc. In some implementations, the signal bearing medium 1002 may encompass a recordable medium 1010, such as, but not limited to, memory, read/write (R/W) CDs, R/W DVDs, etc. In some implementations, signal bearing medium 1002 may encompass a communications medium 1006, such as, but not limited to, a digital and/or an analog communication medium (e.g., a fiber optic cable, a waveguide, a wired communications link, a wireless communication link, etc.).

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method to determine a position of a probe in a surgical site with a plurality of reference structures, comprising:
   receiving a three-dimensional image of the surgical site generated before the probe enters the surgical site, wherein the three-dimensional image is associated with a first coordinate system;
   receiving a first two-dimensional image generated by the probe from a position within the surgical site, wherein the first two-dimensional image is associated with a second coordinate system;
   acquiring registration to the plurality of reference structures based on the first two-dimensional image to obtain a permissible set of probe pose parameters;
   extracting a second two-dimensional image from the three-dimensional image based on the permissible set of probe pose parameters; and
   computing a correlation between the first two-dimensional image and the extracted second two-dimensional image to map the position of the probe represented by the second coordinate system to a position represented by the first coordinate system with respect to the three-dimensional image.

2. The method of claim 1, wherein the acquiring registration comprises:
   setting a first set of probe pose parameters and a first set of search parameters;
   searching for a first of the plurality of reference structures in the first two-dimensional image based on the first set of probe pose parameters and the first set of search parameters; and
   determining whether the first set of probe pose parameters result in finding agreement between the first of the plurality of reference structures represented in the first two-dimensional image and the first of the plurality of reference structures represented in the three-dimensional image.

3. The method of claim 2, further comprising setting a second set of search parameters to search for a second of the plurality of reference structures in the first two-dimensional image.

4. The method of claim 1, wherein the computing of the correlation comprises:
   selecting a first set of pixels representing tissues from the first two-dimensional image;
   selecting a second set of pixels representing tissues from the extracted second two-dimensional image; and
   computing the correlation based on the first set of pixels and the second set of pixels.

5. The method of claim 1, further comprising applying a spatial bandpass filter to the first two-dimensional image before the computing of the correlation.

6. The method of claim 1, further comprising applying a spatial bandpass filter to the extracted second two-dimensional image before the computing of the correlation.

7. The method of claim 1, further comprising applying a spatial bandpass filter to the three-dimensional image before the extracting of the second two-dimensional image.

8. The method of claim 1, further comprising filtering out speckle artifact in the first two-dimensional image before the computing of the correlation.

9. The method of claim 1, wherein the probe is limited to move linearly in the surgical site.

10. The method of claim 1, wherein the probe is limited to rotate about its axis in the surgical site.

11. A non-transitory machine readable medium embodying a set of executable instructions for a method to determine a position of a probe in a surgical site with a plurality of reference structures, which in response to execution by a computing device, cause the computing device to:
   receive a three-dimensional image of the surgical site generated before the probe enters the surgical site, wherein the three-dimensional image is associated with a first coordinate system;
   receive a first two-dimensional image generated by the probe from a position within the surgical site, wherein the first two-dimensional image is associated with a second coordinate system;
   acquire registration to the plurality of reference structures based on the first two-dimensional image to obtain a permissible set of probe pose parameters;
   extract a second two-dimensional image from the three-dimensional image based on the permissible set of probe pose parameters; and
   compute a correlation between the first two-dimensional image and the extracted second two-dimensional image to map the position of the probe represented by the second coordinate system to a position represented by the first coordinate system with respect to the three-dimensional image.

12. The non-transitory machine readable medium of claim 11, wherein the acquiring registration comprises:
   setting a first set of probe pose parameters and a first set of search parameters;
   searching for a first of the plurality of reference structures in the first two-dimensional image based on the first set of probe pose parameters and the first set of search parameters; and
   determining whether the first set of probe pose parameters result in finding agreement between the first of the plurality of reference structures represented in the first two-dimensional image and the first of the plurality of reference structures represented in the three-dimensional image.

13. The non-transitory machine readable medium of claim 12, further embodying a set of executable instructions, which in response to execution by the computing device, cause the computing device to set a second set of search parameters to search for a second of the plurality of reference structures in the first two-dimensional image.

14. The non-transitory machine readable medium of claim 11, wherein the computing of the correlation comprises:
   selecting a first set of pixels representing tissues from the first two-dimensional image;
   selecting a second set of pixels representing tissues from the extracted second two-dimensional image; and
   computing the correlation based on the first set of pixels and the second set of pixels.

15. The non-transitory machine readable medium of claim 11, further embodying a set of executable instructions, which in response to execution by the computing device, cause the computing device to apply a spatial bandpass filter to the first two-dimensional image before the computing of the correlation.

16. The non-transitory machine readable medium of claim 11, further embodying a set of executable instructions, which in response to execution by the computing device, cause the computing device to apply a spatial bandpass filter to the extracted second two-dimensional image before the computing of the correlation.

17. The non-transitory machine readable medium of claim 11, further embodying a set of executable instructions, which in response to execution by the computing device, cause the computing device to apply a spatial bandpass filter to the three-dimensional image before the extracting of the second two-dimensional image.

18. The non-transitory machine readable medium of claim 11, further embodying a set of executable instructions, which in response to execution by the computing device, cause the computing device to filter out speckle artifact in the first two-dimensional image before the computing of the correlation.

19. The non-transitory machine readable medium of claim 11, wherein the probe is limited to move linearly in the surgical site.

20. The non-transitory machine readable medium of claim 11, wherein the probe is limited to rotate about its axis in the surgical site.

21. A system configured to determine a position of a probe in a surgical site with a plurality of reference structures, comprising:
   a processor;
   a first table and a second table; and
   a memory embodying a set of executable instructions, which in response to execution by the processor, cause the processor to
   acquire registration to the plurality of reference structures based on a first two-dimensional image generated by the probe from a position within the surgical site during a surgical procedure and a three-dimensional image of the surgical site before the surgical procedure to obtain a permissible set of probe pose parameters, wherein the three-dimensional image is associated with a first coordinate system, and the first two-dimensional image is associated with a second coordinate system,
   extract a second two-dimensional image from the three-dimensional image based on the permissible set of probe pose parameters,
   select a first set of pixels from the first two-dimensional image using the first table, select a second set of pixels from the extracted second two-dimensional image using the first table and the second table and based on one of the permissible set of probe pose parameters, and compute a correlation between the first set of pixels and the second set of pixels to map the position of the probe represented by the second coordinate system to a position represented by the first coordinate system with respect to the three-dimensional image.

22. The system of claim 21, wherein the memory embodying additional executable instructions, which in response to execution by the processor, cause the processor to exclude pixels representing bone from the second set of pixels before computing the correlation.

23. The system of claim 21, wherein the first table comprises a list of memory addresses of the first set of pixels, and the list follows a raster scan order.

24. The system of claim 21, wherein at least some of the permissible set of probe pose parameters are inputs to the second table.

* * * * *